(12) United States Patent
Chang

(10) Patent No.: US 11,351,054 B2
(45) Date of Patent: *Jun. 7, 2022

(54) MULTILAYER FILM INCLUDING FOAM LAYER AND OSTOMY PRODUCTS MADE THEREFROM

(71) Applicant: Hollister Incorporated, Libertyville, IL (US)

(72) Inventor: Moh-Ching Oliver Chang, Lake in the Hills, IL (US)

(73) Assignee: Hollister Incorporated, Libertyville, IL (US)

( * ) Notice: Subject to any disclaimer, the term of this patent is extended or adjusted under 35 U.S.C. 154(b) by 617 days.

This patent is subject to a terminal disclaimer.

(21) Appl. No.: 16/294,135

(22) Filed: Mar. 6, 2019

(65) Prior Publication Data

US 2019/0231581 A1 Aug. 1, 2019

Related U.S. Application Data

(63) Continuation of application No. 13/835,499, filed on Mar. 15, 2013, now Pat. No. 10,322,024.

(Continued)

(51) Int. Cl.
*A61F 5/44* (2006.01)
*A61L 28/00* (2006.01)
(Continued)

(52) U.S. Cl.
CPC ............ *A61F 5/4404* (2013.01); *A61F 5/441* (2013.01); *A61L 28/0026* (2013.01); *A61L 28/0053* (2013.01); *B32B 5/18* (2013.01); *B32B 5/32* (2013.01); *B32B 7/12* (2013.01); *B32B 27/065* (2013.01); *B32B 27/08* (2013.01); *B32B 27/302* (2013.01); *B32B 27/32* (2013.01); *A61L 2420/08* (2013.01); *B32B 2266/025* (2013.01); *B32B 2266/0207* (2013.01); *B32B 2270/00* (2013.01); *B32B 2307/102* (2013.01); *B32B 2307/536* (2013.01); *B32B 2307/702* (2013.01);
(Continued)

(58) Field of Classification Search
CPC combination set(s) only.
See application file for complete search history.

(56) References Cited

U.S. PATENT DOCUMENTS 4,376,799 A * 3/1983 Tusim .................... B32B 27/08
604/339
5,407,713 A 4/1995 Wilfong et al.
(Continued)

FOREIGN PATENT DOCUMENTS

EP 0958916 A2 11/1999
JP 2000255008 A 9/2000
(Continued)

*Primary Examiner* — Guy K Townsend
(74) *Attorney, Agent, or Firm* — Levenfeld Pearlstein, LLC

(57) ABSTRACT

An ostomy appliance includes a multilayer composite film comprising at least one foam layer. An outer foam layer can function as a skin contact layer providing comfort and softness characteristics that are comparable to a nonwoven comfort layer. Preferably, at least one foam layer includes a vinyl-bond rich triblock copolymer and provides sound absorbing properties. The multilayer composite film can also include at least one layer comprising a filler to further enhance sound absorbing properties.

20 Claims, 7 Drawing Sheets

Related U.S. Application Data

(60) Provisional application No. 61/755,709, filed on Jan. 23, 2013.

(51) Int. Cl.

| | | |
|---|---|---|
| *B32B 5/32* | (2006.01) | |
| *B32B 7/12* | (2006.01) | |
| *B32B 27/06* | (2006.01) | |
| *B32B 27/32* | (2006.01) | |
| *B32B 5/18* | (2006.01) | |
| *A61F 5/441* | (2006.01) | |
| *B32B 27/08* | (2006.01) | |
| *B32B 27/30* | (2006.01) | |

(52) U.S. Cl.
CPC ... *B32B 2307/7248* (2013.01); *B32B 2439/40* (2013.01); *B32B 2439/80* (2013.01); *B32B 2535/00* (2013.01)

(56) References Cited

U.S. PATENT DOCUMENTS

| | | | |
|---|---|---|---|
| 5,496,295 A | 3/1996 | Wilfong et al. | |
| 5,643,375 A | 7/1997 | Wilfong et al. | |
| 5,722,965 A * | 3/1998 | Kuczynski | A61F 5/443 604/338 |
| 5,730,919 A | 3/1998 | Wilfong et al. | |
| 5,983,604 A | 11/1999 | Wilfong et al. | |
| 6,013,363 A | 1/2000 | Takahashi et al. | |
| 6,451,912 B1 | 9/2002 | Kelch | |
| 6,454,740 B1 * | 9/2002 | Mody | A61M 25/0097 604/95.04 |
| 6,455,161 B1 * | 9/2002 | Regnier | C08J 5/18 428/483 |
| 6,558,809 B1 | 5/2003 | Kelch et al. | |
| 6,559,234 B1 * | 5/2003 | Arai | C08J 9/06 526/170 |
| 6,579,584 B1 | 6/2003 | Compton | |
| 6,946,182 B1 | 9/2005 | Allgeuer et al. | |
| 7,070,852 B1 | 7/2006 | Reiners et al. | |
| 7,270,860 B2 * | 9/2007 | Giori | B32B 27/32 428/34.1 |
| 7,279,532 B2 | 10/2007 | Sasagawa et al. | |
| 7,807,241 B2 * | 10/2010 | Sasagawa | B32B 25/04 428/36.1 |
| 7,993,739 B2 * | 8/2011 | Barger | B32B 5/18 428/318.6 |
| 9,895,255 B2 * | 2/2018 | Chang | B32B 27/34 |
| 10,322,024 B2 * | 6/2019 | Chang | B32B 27/08 |
| 10,470,917 B2 * | 11/2019 | Chang | B32B 27/32 |
| 10,980,661 B2 * | 4/2021 | Chang | B32B 27/065 |
| 2002/0025394 A1 * | 2/2002 | Bradfute | B32B 27/30 428/476.1 |
| 2002/0188065 A1 | 12/2002 | Kelch | |
| 2004/0126524 A1 | 7/2004 | Longo et al. | |
| 2007/0005032 A1 * | 1/2007 | Shan | A61F 5/448 604/342 |
| 2007/0237916 A1 * | 10/2007 | Rasmussen | A61F 5/441 428/521 |
| 2008/0020162 A1 | 1/2008 | Fackler et al. | |
| 2010/0030167 A1 | 2/2010 | Thirstrup et al. | |
| 2010/0121290 A1 | 5/2010 | Rasmussen et al. | |
| 2010/0210745 A1 * | 8/2010 | McDaniel | C09D 7/48 521/55 |
| 2010/0330356 A1 * | 12/2010 | Jokisch | B32B 27/065 428/317.1 |
| 2011/0230850 A1 * | 9/2011 | Stroebech | A61L 24/06 604/344 |
| 2011/0250626 A1 * | 10/2011 | Williams | C12Q 1/61 106/4 |
| 2011/0285048 A1 | 11/2011 | Barger et al. | |
| 2012/0010580 A1 * | 1/2012 | Forbes | A61F 5/441 604/334 |
| 2012/0143155 A1 * | 6/2012 | Edvardsen | A61F 5/443 604/318 |
| 2012/0232504 A1 * | 9/2012 | Chang | A61F 5/445 428/476.1 |
| 2013/0025764 A1 | 1/2013 | Henderson | |
| 2013/0045347 A1 | 2/2013 | Kawasumi et al. | |
| 2013/0143014 A1 | 6/2013 | Kwasumi et al. | |
| 2013/0221564 A1 | 8/2013 | Allegaert et al. | |
| 2013/0310782 A1 * | 11/2013 | Chang | A61F 5/445 604/333 |
| 2014/0205828 A1 * | 7/2014 | Chang | B32B 27/304 428/317.1 |
| 2014/0207094 A1 * | 7/2014 | Chang | A61F 5/441 604/339 |
| 2014/0221950 A1 * | 8/2014 | Chang | A61L 28/0026 252/62 |
| 2014/0221951 A1 * | 8/2014 | Chang | A61F 5/445 604/332 |
| 2014/0371698 A1 * | 12/2014 | Chang | B32B 27/12 181/294 |
| 2017/0042722 A1 * | 2/2017 | Chang | B32B 7/12 |
| 2018/0125696 A1 * | 5/2018 | Chang | B32B 27/306 |
| 2019/0231581 A1 * | 8/2019 | Chang | A61L 28/0026 |

FOREIGN PATENT DOCUMENTS

| | | |
|---|---|---|
| JP | 02000504 A | 1/2002 |
| JP | 2003025518 A | 1/2003 |
| JP | 2003503572 A | 1/2003 |
| JP | 2005255830 A | 9/2005 |
| JP | 2006280843 A | 10/2006 |
| WO | 0100408 A1 | 1/2001 |
| WO | 0100716 A2 | 1/2001 |
| WO | 2007093186 A | 8/2007 |
| WO | 2007110080 A | 10/2007 |
| WO | 2009087877 A1 | 7/2009 |
| WO | 2013102009 A1 | 7/2013 |
| WO | 2014116444 A1 | 7/2014 |

\* cited by examiner

MULTILAYER FILM INCLUDING FOAM LAYER AND OSTOMY PRODUCTS MADE THEREFROM

CROSS-REFERENCE TO RELATED APPLICATION DATA

This application is a continuation of U.S. patent application Ser. No. 13/835,499, filed Mar. 15, 2013, which claims the benefit of and priority to U.S. Provisional Application No. 61/755,709, filed Jan. 23, 2013, the disclosures of which are incorporated herein by reference.

BACKGROUND

The present disclosure relates to multilayer films for ostomy products, and more particularly to multilayer films including a foamed layer having sound absorbing properties.

Ostomy appliances for collecting body waste, such as ostomy pouches, are used by patients who have had surgery such as a colostomy, ileostomy, or urostomy. Typically, an ostomy pouch includes two opposing walls, which are sealed around peripheral edges to define a cavity to collect body waste. Nonwovens have been commonly used with odor barrier films to make ostomy pouches. One example is a "3-layer" ostomy pouch including two layers of odor barrier films forming the opposing walls, and a nonwoven layer attached to the body side wall of the ostomy pouch. The nonwoven functions as a comfort panel to give soft touch feel to users and to reduce the wet slippery feel when the user perspires. Another example is a "4-layer" ostomy pouch including two layers of odor barrier films forming the opposing walls and two nonwoven layers, one attached to each of the walls.

Although nonwovens provide added comfort for users, there are some challenges in making ostomy pouches with nonwovens. For example, thickness variances for nonwovens are relatively greater than polymer films, which present process challenges in making ostomy pouches. Further, the process of maintaining consistent tension between a nonwoven and a film, and providing sufficient and precise energy to heat seal the nonwoven and the film are typically more complicated than between two polymeric films. Furthermore, the relatively high cost of nonwovens increases the cost to manufacture ostomy pouches which may result in increased costs to the user.

Another disadvantage of using nonwoven for ostomy pouches is that water can permeate through the nonwoven layer when a user takes a shower or swims. Further, when the nonwoven layer and the film layer are not laminated together, for example, sealed around their respective perimeters, the nonwoven layer is not very effective in reducing film noise.

In addition to providing comfort and softness, it is also highly desirable that ostomy pouches do not make noise during use for obvious reasons. Ostomy pouches that include a quiet film to reduce the noise produced by the pouches, for example, the plastic crackling sound made by the pouch when a user moves around, have been developed. Examples of such a quiet film include the multilayer films disclosed in Giori, U.S. Pat. No. 7,270,860, which is assigned to the assignee of the present application and incorporated herein in its entirety by reference.

When body waste is released from a stoma, flatus gas is often released together with the waste. The flatus gas passing through the stoma can cause a vibratory transient in body tissue, which is uncontrollable by the patient. Such release of the flatus gas from the stoma can accompany indiscreet noise, which can cause embarrassment to the patient. Conventional quiet films, however, could be improved upon to better insulate the flatus noise to prevent embarrassment.

Because of the inherent severe medical, social, and personal concerns related to the need for use of an ostomy appliance, improvements in ostomy appliances are desired. Any appreciable improvement in such ostomy appliances to provide greater discretion, privacy and comfort is of great importance in the quality of life of the increasing number of ostomy patients. The present disclosure provides improved ostomy appliances including a foam material that can replace conventional nonwoven layers according to various embodiments, to provide comfort and enhanced sound insulating properties.

BRIEF SUMMARY

Ostomy pouches are made using a multilayer composite film including at least one foam layer according to various embodiments of the present disclosure. The at least one foam layer includes an outer foam layer which can function as a skin contact layer providing comfort and softness characteristics that are comparable to the nonwoven comfort layer of prior art ostomy pouches. Preferably, the at least one foam layer comprises a vinyl-bond rich triblock copolymer to provide sound absorbing properties.

In one aspect, an ostomy pouch including an outer wall and a bodyside wall is provided. The outer wall and the bodyside wall are sealed along their peripheral edges to define a cavity. The bodyside wall is formed of a composite film including an outer foam layer which is in contact with user's skin when the ostomy pouch is attached to the user. Further, the composite film includes a seal layer and an odor barrier layer.

In one embodiment, the composite film has a six layer construction including seal layer/tie layer/odor barrier layer/tie layer/inner foam layer/outer foam layer. In another embodiment, the composite film has a seven layer construction including seal layer/tie layer/odor barrier layer/tie layer/foam layer/foam layer/outer foam layer. The layers of the composite film are coextruded. Preferably, at least one of the foam layers includes a vinyl-bond rich triblock copolymer. For example, each of the foam layers can be formed from a blend comprising a non-hydrogenated vinyl-bond rich styrene-isoprene-styrene block copolymer and an ethylene methyl acrylate copolymer (EMA). Alternatively, each of the foam layers can be formed from a blend comprising a hydrogenated vinyl-bond rich styrene-isoprene-styrene block copolymer and an EMA copolymer.

In another aspect, a sound insulating ostomy pouch including a first wall and a second wall is provided. The first wall and the second wall are sealed along their peripheral edges to define a cavity. At least one of the first wall and the second wall is formed of a composite film including at least one foam layer comprising a vinyl-bond rich triblock copolymer. For example, the at least one foam layer can be formed from a blend comprising a non-hydrogenated vinyl-bond rich styrene-isoprene-styrene block copolymer and an EMA copolymer. In another example, the at least one foam layer can be formed from a blend comprising a hydrogenated vinyl-bond rich styrene-isoprene-styrene block copolymer and an EMA copolymer. Further, the composite film includes a seal layer and an odor barrier layer.

In one embodiment, the composite film has a six layer construction including seal layer/tie layer/odor barrier layer/tie layer/inner foam layer/outer foam layer. In a different embodiment, the composite film has a seven layer construction including seal layer/tie layer/odor barrier layer/tie layer/foam layer/foam layer/outer foam layer. The layers of the composite film are coextruded.

The at least one foam layer includes an outer foam layer, and the sound insulated ostomy pouch is configured such that the outer foam layer is in contact with user's skin when the sound insulated ostomy pouch is attached to the user. The outer foam layer comprises a slip agent.

In another embodiment, each of the first wall and the second wall is formed of a composite film including at least one foam layer comprising a vinyl-bond rich triblock copolymer.

The composite film according to any of the above discussed embodiments can also include at least one layer comprising filler to further enhance sound absorbing properties of the composite film. For example the composite film can include a seal layer comprising mica, barium sulfate, or talc.

In yet another aspect, a sound insulating composite film including at least one foam layer comprising a vinyl-bond rich triblock copolymer is provided. The at least one foam layer may be formed from a blend comprising a non-hydrogenated vinyl-bond rich styrene-isoprene-styrene block copolymer and an EMA copolymer, or a blend comprising a hydrogenated vinyl-bond rich styrene-isoprene-styrene block copolymer and an EMA copolymer.

In one embodiment, the composite film also includes a seal layer and an odor barrier layer. For example, the composite film can have a six layer construction including seal layer/tie layer/odor barrier layer/tie layer/inner foam layer/outer foam layer, or a seven layer construction including seal layer/tie layer/odor barrier layer/tie layer/foam layer/foam layer/outer foam layer. Further, the composite film can also include at least one layer comprising mica, barium sulfate, or talc. For example, the composite film can include a seal layer comprising mica, barium sulfate, or talc.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
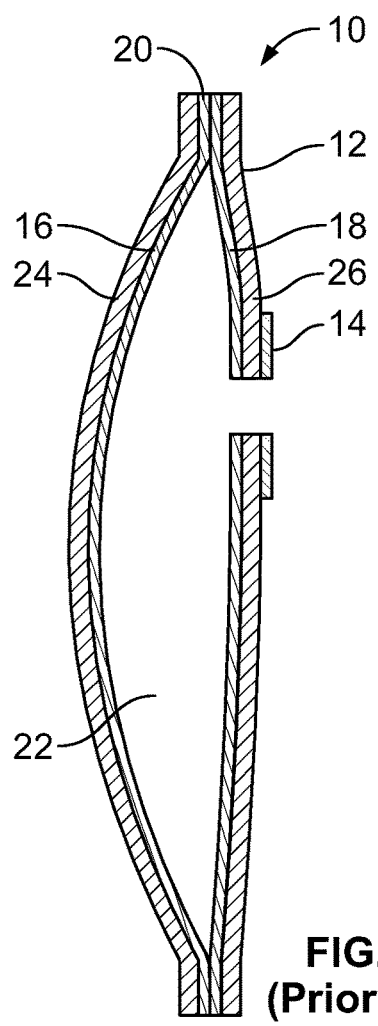
FIG. 1 is a cross-sectional illustration of a prior art ostomy appliance.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

FIG. 1 is a cross-sectional illustration of a prior art one-piece ostomy pouch 10. The ostomy pouch 10 generally includes a pouch 12 and a skin barrier 14. The pouch 12 includes first and second opposing walls 16, 18, which are sealed around peripheral edges 20 thereof to define a cavity 22 for collecting body waste. The pouch 12 also includes a first nonwoven layer 24 attached to the first wall 16, and a second nonwoven layer 26 attached to the second wall 18. The nonwoven layers 24, 26 are attached to the respective walls 16, 18 via heat sealing or an adhesive. Each of the first and second walls 16, 18 is formed of a suitable odor barrier film, which may be a single layer film or a multilayer film.

Typically, each side of the pouch is configured to have a total thickness of about 10 mil to about 12 mil. For example, each side includes a nonwoven layer heat sealed to a wall, in which the wall has a thickness of about 3 mil and the nonwoven layer has a thickness of about 8 mil to provide a total thickness of about 11 mil. In another example, each side includes a nonwoven layer attached to a wall by an adhesive therebetween, in which the wall has a thickness of about 2.25 mil, and the adhesive has a thickness of about 1.1 mil, and the nonwoven layer has a thickness of about 8 mil to provide a total thickness of about 11.35 mil.

Figure 2:
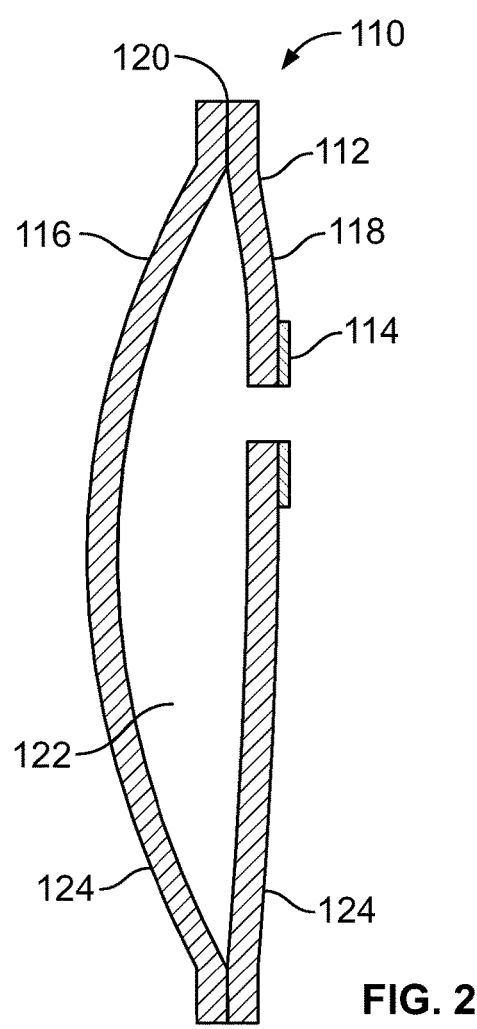
FIG. 2 is a cross-sectional illustration of an ostomy pouch according to an embodiment of the present disclosure.

FIG. 2 is a cross-sectional illustration of an embodiment of a one-piece ostomy pouch 110. The ostomy pouch 110 is similarly configured to the ostomy pouch 10 of FIG. 1, and generally includes a pouch 112 and a skin barrier 114. The pouch 112 includes first and second opposing walls 116, 118, which are sealed around peripheral edges 120 thereof by heat sealing or by any other suitable means to define a cavity 122 therebetween for collecting body waste.

Each of the first and second walls 116, 118 is formed of a multilayer composite film 124. The composite film 124 is designed to replace the film/nonwoven construction or the film/adhesive/nonwoven construction of prior art pouches. The composite film 124 includes at least one odor barrier film layer and at least one foam layer, which are coextruded. Thus, manufacturing processes of the pouch can be simplified by reducing number of suppliers required for film, nonwoven and adhesive, and eliminating steps for laminating or heat sealing the layers, which in turn provides cost savings. The foam layer of the composite film is configured to have softness sufficient for skin contact to replace the nonwoven layer of prior art pouches. The foam layer can be configured to have a skin contact quality soft feel by using rubbery resins and fine foam cells. Preferably, the foam layer also provides sound absorbing characteristics.

Preferably, the composite film 124 is configured to have a thickness similar to the total thickness of the film/nonwoven construction or the film/adhesive/nonwoven construction of prior art ostomy pouches. For example, the composite film 124 has an overall thickness of about 10 mil to about 12 mil. The composite film 125 can also be configured to have thinner thicknesses, for example, about 7 mil, to provide a lower cost composite film which still has similar softness and film characteristics as the thicker composite films. In some embodiments, the first wall 116 and the second wall 118 can be formed of different composite films, or only one of the first and second walls 116, 118 can be formed of a composite film.

Figure 3:
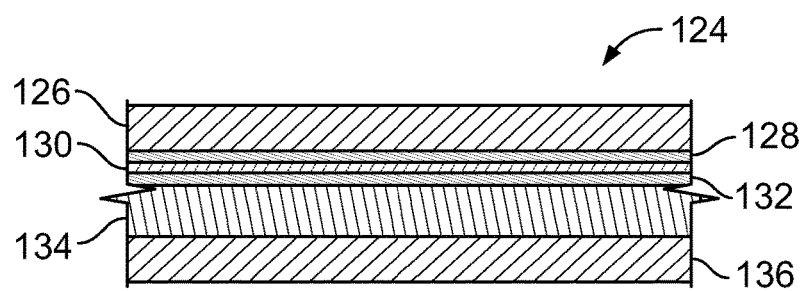
FIG. 3 is a cross-sectional illustration of a six-layer composite film according to an embodiment.

FIG. 3 is a cross-sectional illustration of an embodiment of the composite film 124. The composite film 124 has a six-layer construction including a seal layer 126, tie layers 128, 132, a barrier layer 130, and foam layers 134, 136. In this embodiment, the composite film 124 has the structure ABCBDE, where A represents the seal layer, B represents the tie layers, C represents the barrier layer, D represents an inner foam layer, and E represents an outer foam layer.

Figure 6:
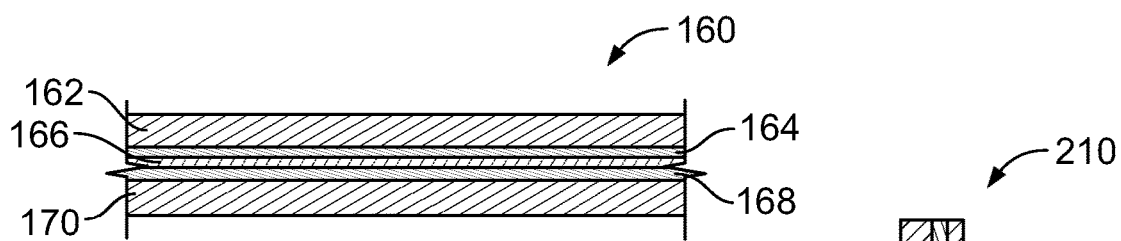
FIG. 6 is a cross-sectional illustration of a five-layer composite film according to an embodiment.

In other embodiments, the composite film can include more than six layers or less than six layers. For example, a composite film can have a five-layer construction including a barrier layer, two tie layers, a seal layer, and one foam layer (i.e. ABCBE). FIG. 6 is a cross-sectional illustration of a five-layer composite film embodiment including a seal layer 162, tie layers 164, 168, a barrier layer 166, and a foam layer 170. The composite film 160 has a seal/tie/barrier/tie/foam construction. Alternatively, a composite film can have a seven-layer construction including a barrier layer, two tie layers, a seal layer, and three foam layer (e.g. ABCBDDE).

The seal layer 126 is formed of a material having suitable heat sealability, such that the seal layers of the first and second walls 116, 118 can be heat sealed along their perimeter to form the pouch 112. Suitable materials for the seal layer 126 include copolymers of ethylene with vinyl esters, such as vinyl acetate copolymer (EVA) and copolymers of ethylene methyl acrylate (EMA). Suitable EVA copolymers can contain about 10 wt. % to 35 wt. % vinyl acetate and more preferably, about 18 wt. % vinyl acetate, by weight of the copolymer. One such material is available from Exxon-Mobil as product Escorene® Ultra FL00218. Such a material has a melting point temperature of 86° C. and a Shore A hardness of about 91. EVA is known to exhibit the necessary characteristics for joining to another EVA member, as by heat sealing, to provide an air-tight, liquid-tight seal at the joint or seal. EVA materials can be blended to facilitate formation and film extrusion. For example, an EVA blend can have about 98 percent by weight (wt. %) EVA with about 2 wt. % anti-block and slip additives, in an EVA carrier. One suitable additive is available from A. Schulman Inc., as Polybatch® SAB-1982VA.

Suitable EMA copolymers can include about 10 wt. % to about 35 wt. % of the methyl acrylate and preferably about 18.5 wt. % to about 30 wt. % methyl acrylate. Such EMA copolymers typically have melting point temperatures of about 85° C. to 87° C. and a Shore A hardness of about 73 and Shore D hardness of about 20 to 25. Such materials are available from Arkema Inc. as Lotryl® 18AM02 and from DuPont as Elvaloy® 1330AC. The EMA resins can also be blended with anti-block and slip additives in an EVA carrier. One suitable material for blending is the aforementioned Polybatch® SAB-1982VA. Such a blend can have, for example EMA at about 98 wt. %, with about 2 wt. % Polybatch® SAB-1982VA anti-block and slip additive.

The seal layer 126 can also be formed of blends of EVA copolymer (e.g. Escorene® FL00218 present at 49 wt. %) and PP-elastomer (e.g. Versify® 2200 present at 49 wt. %) with anti-block and slip additives, or blends of EMA copolymer (e.g. Elvaloy® 1330AC present at 49 wt. %) and PP-elastomer (e.g. Versify® 2200 present at 49 wt. %) also with anti-block and slip additives. PP-elastomers such as Versify® from Dow, Vistamaxx® from Exxon, and Notio® from Mitsui are also suitable.

In addition to heat sealability, the seal layer 126 can also provide sound absorbing properties. In such an embodiment, the seal layer 126 can comprise a vinyl-bond rich triblock copolymer, such as Hybrar®, to enhance sound absorbing properties and mechanical properties of the composite film. For example, the seal layer 126 can be formed from a blend of a non-hydrogenated styrene isoprene copolymer (Hybrar® 5127), a PP-elastomer (Vistamaxx®), and an EMA (Lotryl® 20MA08).

On either side of the barrier layer 130 are the tie layers 128, 132. The tie layers facilitate adhesion of the barrier layer 130 to the remainder of the composite film structure. The seal layer 126 and the inner foam layer 134 are adjacent to the tie layers 128, 132, respectively. The tie layers 128, 132 can be formed of the same material or different materials. Suitable materials for the ties layers 128, 132 include maleated polyolefins, such as a maleated ethylene methyl acrylate copolymers having maleic anhydride present at about 0.3 wt. % and methyl acrylate present at about 20 wt. % of the resin. One such material is available from Arkema, Inc. as Lotader® 4503.

The barrier layer 130 can be formed from various materials having gas barrier properties. Preferably, the barrier layer 130 is formed from a non-chlorine containing polymer that is substantially impermeable to malodor causing compounds typically encountered in ostomy pouches. Such malodor causing compounds can include sulfur containing compounds and indoles. Suitable barrier layer materials include resins such as amorphous polyamide (nylon) resin, and an anhydride-modified olefinic polymer or copolymer, or an epoxy modified olefin polymer or copolymer. For example, the barrier layer 130 can be formed from a blend of an amorphous polyamide, such as Selar® PA3426R, by DuPont Company, and a functionalized rubber blend or compound, such as Lotader® 4720.

The inner foam layer 134 and the outer foam layer 136 can be formulated from the same material or different materials. For example, the inner foam layer 134 can be formed from a polyolefin with a blowing agent and a color additive, and the outer foam layer 136 can be formed from the same polyolefin with a blowing agent, and slip and antiblock agents. Ethylene based polymers, such as copolymers of ethylene with vinyl esters, e.g. EVA and EMA, ethylene-octene (EO) plastomers, and ethylene-propylene (EP) copolymers (PP-elastomer) are suitable for the foam layers. One suitable material is an ethylene vinyl acetate (EVA) copolymer having a vinyl acetate content of about 8 wt. % to 30 wt. %, and preferably about 10 wt. % to about 25 wt. %, a melting point temperature of about 86° C. and a Shore A hardness of about 91, such as Escorene® FL00218, available from ExxonMobil Corporation. Suitable EMA copolymers can include about 10 wt. % to about 35 wt. % methyl acrylate and preferably about 18.5 wt. % to about 30 wt. % methyl acrylate. Such EMA copolymers typically have melting point temperatures of about 85° C. to 87° C., a Shore A hardness of about 73 and Shore D hardness of about 20 to 25. Such materials are available from Arkema Inc. as Lotryl® 18AM02 and from DuPont as Elvaloy® 1330AC.

Another suitable material is an EO plastomer having a melting point temperature of about 95° C. and specific gravity of about 0.902, such as Exact® 0203 resin, also available from ExxonMobil Corporation, which has a specific gravity of about 0.88 and a Shore A hardness of about 95. Still another suitable resin is an ethylene-propylene copolymer (PP-elastomer) resin. It has excellent compatibility with polypropylene (PP) and polyethylene (PE). One such material is available from Dow Chemical as Versify® 2200. This resin has melting point of about 82° C., a Shore A hardness of 94 and a Shore D hardness of 42. It has a specific gravity of 0.878. Blends of various PP copolymer resins are also suitable, for example, blends of Versify® 2200 and Versify® 3400, which is a similar PP copolymer resin, but has a higher melting point of about 97° C., a Shore A hardness of 72 and a Shore D hardness of 22, and a specific gravity of about 0.865. Suitable blends can have ratios of about 50 percent of Versify® 2200 to about 75 percent of Versify® 2200 by weight of the blend. PP-elastomers such as Versify® from Dow, Vistamaxx® from Exxon, and Notio® from Mitsui, and blends thereof are also suitable.

Preferably, the foam layers 134, 136 also provide at least some sound absorbing properties. In such an embodiment, each of the foam layers 134, 136 comprises a vinyl-bond rich triblock copolymer, such as Hybrar® from Kuraray Co. Ltd., to enhance mechanical properties and sound absorbing properties of the composite film. For example, each of the foam layers can be formed from a blend comprising a non-hydrogenated vinyl-bond rich styrene-isoprene-styrene (SIS) block copolymer, e.g. Hybrar® 5125 and 5127, or a hydrogenated vinyl-bond rich styrene-isoprene-styrene (SIS) block copolymer, e.g. Hybrar® 7125, and at least one other polymer, such as EMA (e.g. Lotryl® 20MA08).

In one embodiment, the six-layer composite film 124 has a total thickness of about 280 µm (11 mil), in which the seal layer 126 has a thickness of about 64 µm, each of the tie layers 128, 132 has a thickness of about 4 µm, the barrier layer 130 has a thickness of about 4 µm, the inner foam layer 134 has a thickness of about 140 µm, and the outer foam layer 136 has a thickness of about 64 µm.

In this embodiment, the seal layer 126 is formed a blend comprising about 49 wt. % of EVA copolymer (Escorene® FL00218), about 49 wt. % of PP-elastomers (Vistamaxx® 3980FL), and about 2 wt. % of a slip and antiblock agent (Polybatch® SAB-1982VA). Each of the tie layers 128, 132 is formed from a blend comprising about 80 wt. % EMA (Lotryl® 18MA02) and about 20 wt. % MAH grafted LLDPE (Bynel® CXA41E710). The barrier layer is formed from a blend comprising about 85 wt. % amorphous polyamide (Selar® PA3426R) and 15 wt. % functionalized rubber blend (Lotader® 4720). The inner foam layer 134 is formed from a blend comprising about 45 wt. % of EVA copolymer (Escorene® FL00218), about 45 wt. % of PP-elastomers (Vistamaxx® 3980FL), about 8 wt. % of color masterbatch, and about 2 wt. % of blowing agent (Safoam® FP-40 from Reedy International). The outer foam layer 136 is formed from a blend comprising about 48 wt. % of EVA copolymer (Escorene® FL00218), about 48 wt. % of PP-elastomers (Vistamaxx® 3980FL), about 2 wt. % of blowing agent (Safoam® FP-40), and about 2 wt. % of slip and antiblock agent (Polybatch® SAB-1982VA). The foam layers 134, 136, particularly the outer foam layer 136, include fine foam cells for soft skin touch feel. Further, the slip agent is added to the blend for the outer foam layer 136 to improve the smooth sleek feel of the foam.

Preferably, the foam layers provide sound absorbing properties in addition to a smooth soft feel for improved comfort for wearers. Thus, at least one foam layer comprises a vinyl-bond rich triblock copolymer such as a non-hydrogenated vinyl-bond rich styrene-isoprene-styrene (SIS) block copolymer, e.g. Hybrar® 5125 and 5127, or a hydrogenated vinyl-bond rich styrene-isoprene-styrene (SIS) block copolymer, e.g. Hybrar® 7125.

In one embodiment, the six-layer composite film 124 has a total thickness of about 288 µm (11.3 mil), in which the seal layer 126 has a thickness of about 20 µm, each of the tie layers 128, 132 has a thickness of about 3 µm, the barrier layer 130 has a thickness of about 4 µm, the inner foam layer 134 has a thickness of about 238 µm, and the outer foam layer 136 has a thickness of about 20 µm.

In this embodiment, the seal layer 126 is formed from a blend comprising about 49 wt. % of EVA copolymer (Escorene® FL00218), about 49 wt. % of PP-elastomers (Vistamaxx® 3980FL), and about 2 wt. % of a slip and antiblock agent (Polybatch® SAB-1982VA). Each of the tie layers 128, 132 is formed from a blend comprising about 80 wt. % EMA (Lotryl® 18MA02) and about 20 wt. % MAH grafted LLDPE (Bynel® CXA41E710). The barrier layer 130 is formed from a blend comprising about 85 wt. % amorphous polyamide (Selar® PA3426R) and 15 wt. % functionalized rubber blend (Lotader® 4720). The inner foam layer 134 is formed from a blend comprising about 47 wt. % of hydrogenated vinyl-bond rich styrene-isoprene-styrene block copolymer (Hybrar® 7125), about 47 wt. % of EMA (Lotryl® 20MA08), about 4 wt. % of color masterbatch, and about 2 wt. % of blowing agent (Safoam® FP-20). The outer foam layer 136 is formed from a blend comprising about 48 wt. % of hydrogenated vinyl-bond rich styrene-isoprene-styrene block copolymer (Hybrar® 7125), about 48 wt. % of EMA (Lotryl® 20MA08), about 2 wt. % of blowing agent (Safoam® FP-20), and about 2 wt. % of slip and antiblock agent (Polybatch® SAB-1982VA). Preferably, the foam layers 134, 136 include fine foam cells for soft smooth feel, and open cell structure to maximize sound absorbing properties of the foam layers. Further, the slip agent is added to the blend for the outer foam layer 136 for improved smooth sleek feel of the foam.

In another embodiment, the six-layer composite film 124 has a total thickness of about 288 µm (11.3 mil), in which the seal layer 126 has a thickness of about 20 µm, each of the tie layers 128, 132 has a thickness of about 3 µm, the barrier layer 130 has a thickness of about 40 µm, the inner foam layer 134 has a thickness of about 202 µm, and the outer foam layer 136 has a thickness of about 20 µm. In this embodiment, the barrier layer 130 is formed from a low melting point nylon, and thus, a non-hydrogenated vinyl-bond rich styrene-isoprene-styrene block copolymer (Hybrar® 5125 or 5127), which has a lower melting point than the hydrogenated vinyl-bond rich styrene-isoprene-styrene block copolymer (Hybrar® 7125), can be used for the foam layers 134, 136. In the previously described embodiment, the amorphous polyamide (Selar® PA3426R) used for the barrier layer has a relatively high melt flow temperature, thus requires a relatively high processing temperature. Therefore, the hydrogenated vinyl-bond rich styrene-isoprene-styrene block copolymer, which has a higher melting point temperature, and is thus more heat stable than the non-hydrogenated vinyl-bond rich styrene-isoprene-styrene block copolymer, was selected for the foam layers. The non-hydrogenated vinyl-bond rich styrene-isoprene-styrene block copolymers can provide additional cost benefits and improved sound absorbing properties in some embodiments.

In this embodiment, the seal layer 126 is formed from a blend comprising about 59 wt. % of EMA (Lotryl® 20MA08), about 39 wt. % of PP-elastomers (Vistamaxx® 3980FL), and about 2 wt. % of a slip and antiblock agent (Polybatch® SAB-1982VA). Each of the tie layers 128, 132 is formed from a blend comprising about 80 wt. % EMA (Lotryl® 20MA08) and about 20 wt. % MAH grafted LLDPE (Bynel® CXA41E710). The barrier layer 130 is formed from a blend comprising about 85 wt. % low melting point nylon (Grilon® BM13 from EMS-Grivory) and 15 wt. % functionalized rubber blend (Lotader® 4720). The inner foam layer 134 is formed from a blend comprising about 46.5 wt. % of non-hydrogenated vinyl-bond rich styrene-isoprene-styrene block copolymer (Hybrar® 5127), about 46.5 wt. % of EMA (Lotryl® 20MA08), about 5 wt. % of color masterbatch, and about 2 wt. % of blowing agent (Safoam® FP-20). The outer foam layer 136 is formed from a blend comprising about 48 wt. % of non-hydrogenated vinyl-bond rich styrene-isoprene-styrene block copolymer (Hybrar® 5127), about 48 wt. % of EMA (Lotryl® 20MA08), about 2 wt. % of blowing agent (Safoam® FP-20), and about 2 wt. % of slip and antiblock agent (Polybatch® SAB-1982VA). Preferably, the foam layers 134, 136 include fine foam cells for soft smooth feel, and open cell structure to maximize sound absorbing properties of the foam layers. Further, the slip agent is added to the blend for the outer foam layer 136 for an improved smooth sleek feel of the foam.

In some embodiments, a composite film includes at least one layer comprising a filler to provide improved sound absorbing or sound deadening properties. Fillers having a platelet shape, such as mica and talc, are preferred. For example, a composite film having improved sound absorbing properties can include at least one sound absorbing foam layer comprising a vinyl-bond rich triblock copolymer and at least one other layer comprising a filler, such as mica, barium sulfate, and/or talc.

In one embodiment, a six-layer composite film 124 (FIG. 3) includes a seal layer comprising a filler. The composite film has a total thickness of about 288 µm (11.3 mil) including a seal layer 126 having a thickness of about 25 µm, two tie layers 128, 132, each of which having a thickness of about 4 µm, a barrier layer 130 having a thickness of about 4 µm, an inner foam layer 134 having a thickness of about 166 µm, and an outer foam layer 136 having a thickness of about 85 µm. The seal layer 126 is formed from a polymer blend comprising about 33.3 wt. % of a EMA/mica blend (the EMA/mica blend includes about 50 wt. % mica (Suzorite® 60S from Imerys Pigments) and about 50 wt. % EMA (Lotryl® 20MA08)), about 25 wt. % of EMA (Lotryl® 20MA08), about 40 wt. % of PP-elastomers (Vistamaxx® 3980FL), and about 1.7 wt. % of a slip and antiblock agent (Polybatch® SAB-1982VA). Each of the tie layers 128, 132 is formed from a blend comprising about 80 wt. % EMA (Lotryl® 18MA02) and about 20 wt. % MAH grafted LLDPE (Bynel® CXA41E710). The barrier layer 130 is formed from a blend comprising about 85 wt. % amorphous polyamide (Selar® PA3426R) and about 15 wt. % functionalized rubber blend (Lotader® 4720). The inner foam layer 134 is formed from a blend comprising about 55 wt. % of hydrogenated vinyl-bond rich styrene-isoprene-styrene block copolymer (Hybrar® 7125), about 31 wt. % of EMA (EMAC® 2207 from West Lake), about 11 wt. % of color masterbatch, and about 3 wt. % of blowing agent (Expancel® 950MB80 from Akzo). The outer foam layer 136 is formed from a blend comprising about 52 wt. % of hydrogenated vinyl-bond rich styrene-isoprene-styrene block copolymer (Hybrar® 7125), about 43 wt. % of EMA (Lotryl® 20MA08), about 3 wt. % of blowing agent (Expancel® 950MB80), and about 2 wt. % of slip and antiblock agent (Polybatch® SAB-1982VA).

Figure 7:
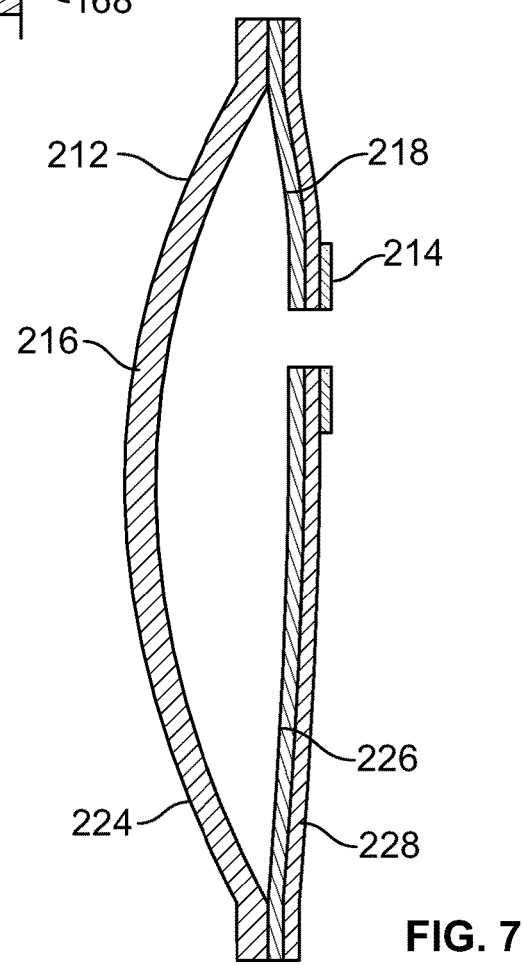
FIG. 7 is a cross-sectional illustration of an ostomy pouch according to another embodiment of the present disclosure.

FIG. 7 is a cross-sectional illustration of a one-piece ostomy pouch 210 according to anther embodiment. The ostomy pouch 210 is similarly configured as the ostomy pouch 110 of FIG. 2, and generally includes a pouch 212 and a skin barrier 214. In this embodiment, a first wall 216 is formed of a composite film 224, and a second wall 218 is formed of a film 226. Further, the ostomy pouch 210 includes a nonwoven layer 228 attached to the second wall 218 to accommodate users who desire characteristics of a nonwoven comfort panel, for example, breathability.

Figure 4:
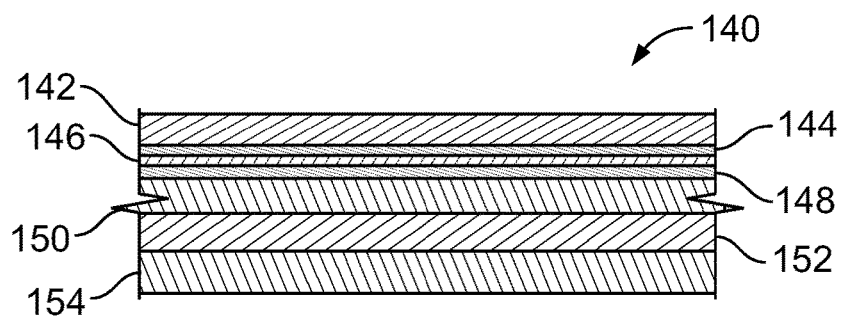
FIG. 4 is a cross-sectional illustration a seven-layer composite film according to an embodiment.

The composite film 224 includes at least one sound absorbing foam layer comprising a vinyl-bond rich triblock copolymer such as a non-hydrogenated vinyl-bond rich styrene-isoprene-styrene (SIS) block copolymer, e.g. Hybrar® 5125 and 5127, or a hydrogenated vinyl-bond rich styrene-isoprene-styrene (SIS) block copolymer, e.g. Hybrar® 7125. The composite film 224 can have any of the multilayer composite constructions discussed in this disclosure. For example, the composite film 224 can have a six-layer construction including a seal layer, two tie layers, a barrier layer, and two foam layers, as shown in FIG. 3. Alternatively, the composite film 224 can have a five-layer construction as shown in FIG. 6 or a seven-layer construction as shown in FIG. 4

The second wall 218 can be formed of a suitable monolayer or multilayer film, such as a composite film including at least one sound absorbing foam layer comprising a vinyl-bond rich triblock copolymer. For example, the film 226 can be the same composite film as the composite film 224 or a different composite film. In one embodiment, the composite film 224 and the film 226 are the same composite film having a six-layer construction of FIG. 3, which includes two foam layers 134, 136 comprising a vinyl-bond rich triblock copolymer. In another embodiment, the film 226 is a different composite film than the composite film 224. For example, the film 226 can be a thinner composite film than the composite film 224. For example, the composite film 224 can have a thickness of about 11 mil, while the film 226 is a composite film having a thickness of about 7 mil.

Alternatively, the film 226 can be a suitable polymeric film, which does not include a foam layer. The film 226 can be a single layer film or a multilayer film. Preferably, the multilayer film includes at least one odor barrier layer. For example, the film 226 can be a six-layer film having a thickness of about 2.24 mil (57 µm) and a seal layer/tie layer/barrier layer/tie layer/inner layer/seal layer construction. In another example, the film 226 can be a seven-layer film having a seal layer/inner layer/tie layer/barrier layer/tie layer/inner layer/seal layer construction. In some embodiments, the multilayer film for the second wall 218 includes at least one layer comprising a vinyl-bond rich triblock copolymer.

Although the embodiments of FIGS. 2 and 7 are a one-piece ostomy appliance with a closed-end pouch, the above discussed multilayer composite films can be used to make other types of ostomy appliances, such as two-piece ostomy appliances and drainable ostomy pouches.

EXAMPLES AND TEST RESULTS

Three composite film samples and a control laminate were prepared and tested for their mechanical and sound absorbing properties. Each of the composite film samples had a total thickness of about 288 µm (11.3 mil) and a seven-layer construction (seal layer/tie layer/barrier layer/tie layer/foam layer/foam layer/foam layer). Each of the foam layers included hydrogenated vinyl-bond rich styrene-isoprene-styrene block copolymer (Hybrar® 7125) for sound absorbing properties. The control laminate, which is currently used in some known ostomy pouches, had a total thickness of about 11.3 mil including a PE nonwoven layer, an adhesive layer, and a multilayer barrier film.

TABLE 1

Composite Film Samples and Control Laminate

| Sample Code | Foam 1 | Foam 2 | Foam 3 | Tie 1 | Barrier | Tie 2 | Seal |
|---|---|---|---|---|---|---|---|
| X3299 | 85 μm 50% Hybrar® 7125 + 46% Lotryl® 20MA08 + 2% Safoam® FP-20 + 2% Polybatch® SAB-1982VA | 83 μm 65% Hybrar® 7125 + 34% EMAC® 2207 + 1% Safoam® FP-20 | 83 μm 65% Hybrar® 7125 + 34% EMAC® 2207 + 1% Safoam® FP-20 | 4 μm 80% Lotryl® 18MA02 + 20% Bynel® CXA41E710 | 4 μm 85% Selar® PA3426R + 15% Lotader® 4720 | 4 μm same as Tie 1 | 25 μm 50% Lotryl® 20MA08 + 48% Vistamaxx® 3980FL + 2% Polybatch® SAB-1982VA |
| X3300 | 85 μm 50% Hybrar® 7125 + 46% Lotryl® 20MA08 + 2% Safoam® FPE-20 + 2% Polybatch® SAB-1982VA | 83 μm 65% Hybrar® 7125 + 34% EMAC® 2207 + 1% Safoam® FPE-20 | 83 μm 65% Hybrar® 7125 + 34% EMAC® 2207 + 1% Safoam® FPE-20 | 4 μm 80% Lotryl® 18MA02 + 20% Bynel® CXA41E710 | 4 μm 85% Selar® PA3426R + 15% Lotader® 4720 | 4 μm same as Tie 1 | 25 μm 50% Lotryl® 20MA08 + 48% Vistamaxx® 3980FL + 2% Polybatch® SAB-1982VA |
| X3301 | 85 μm 50% Hybrar® 7125 + 46% Lotryl® 20MA08 + 2% Expancel® 950MB80 + 2% Polybatch® SAB-1982VA | 83 μm 65% Hybrar® 7125 + 34% EMAC® 2207 + 1% Expancel® 950MB80 | 83 μm 65% Hybrar® 7125 + 34% EMAC® 2207 + 1% Expancel® 950MB80 | 4 μm 80% Lotryl® 18MA02 + 20% Bynel® CXA41E710 | 4 μm 85% Selar® PA3426R + 15% Lotader® 4720 | 4 μm same as Tie 1 | 25 μm 50% Lotryl® 20MA08 + 48% Vistamaxx® 3980FL + 2% Polybatch® SAB-1982VA |

| | Nonwoven | Adhesive | 57 μm (2.24 mil) 6-layer film | | | | |
|---|---|---|---|---|---|---|---|
| Control | 203.2 μm (8 mil) PE nonwoven | 2.8 μm (1.1 mil) adhesive | Seal 97.5% Escorene® FL00218 + 2.5% Polybatch® SAB-1982VA | Inner 87%-89.5% Escorene® FL00218 + 10.5%-13% Schulman® T92030 Beige | Tie 1 80% Lotryl® 18MA02 + 20% Bynel® CXA-41E710 | Barrier 85% Selar® PA3426R + 15% Lotader® 4720 | Tie 2 same as Tie 1 | Seal 97.5% Escorene® FL00218 + 2.5% Polybatch® SAB-1982VA |

As summarized in Table 1, Sample X3299 is a seven-layer composite film 140 (FIG. 4) having a foam layer 1/foam layer 2/foam layer 3/tie layer 1/barrier layer/tie layer 2/seal layer construction. The seal layer 142 has a thickness of about 25 μm, and is formed of a blend comprising about 50 wt. % of EMA (Lotryl® 20MA08), about 48 wt. % of PP-elastomers (Vistamaxx® 3980FL), and about 2 wt. % of a slip and antiblock agent (Polybatch® SAB-1982VA). Each of the tie layer 1 (148) and tie layer 2 (144) has a thickness of about 4 μm, and is formed from a blend comprising about 80 wt. % EMA (Lotryl® 18MA02) and about 20 wt. % MAH grafted LLDPE (Bynel® CXA41E710). The barrier layer 146 has a thickness of about 4 μm, and is formed from a blend comprising about 85 wt. % amorphous polyamide (Selar® PA3426R) and about 15 wt. % functionalized rubber blend (Lotader® 4720). Each of the foam layer 2 (152) and the foam layer 3 (150) has a thickness of about 83 μm, and is formed from a blend comprising about 65 wt. % of hydrogenated vinyl-bond rich styrene-isoprene-styrene block copolymer (Hybrar® 7125), about 34 wt. % of EMA (EMAC® 2207), and about 1 wt. % of blowing agent (Safoam® FP-20). The foam layer 1 (154) has a thickness of about 85 μm, and is formed from a blend comprising about 50 wt. % of hydrogenated vinyl-bond rich styrene-isoprene-styrene block copolymer (Hybrar® 7125), about 46 wt. % of EMA (Lotryl® 20MA08), about 2 wt. % of blowing agent (Safoam® FP-20), and about 2 wt. % of slip and antiblock agent (Polybatch® SAB-1982VA). Thus, the composite film 140 of Sample X3299 has a total thickness of about 288 μm (11.3 mil).

Sample X3300 is also a seven-layer composite film 140 having the same layer construction as SampleX3299, which is illustrated in FIG. 4. The seal layer 142 has a thickness of about 25 μm, and is formed from a blend comprising about 50 wt. % of EMA (Lotryl® 20MA08), about 48 wt. % of PP-elastomers (Vistamaxx® 3980FL), and about 2 wt. % of a slip and antiblock agent (Polybatch® SAB-1982VA). Each of the tie layer 1 (148) and tie layer 2 (144) has a thickness of about 4 μm, and is formed from a blend comprising about 80 wt. % EMA (Lotryl® 18MA02) and about 20 wt. % MAH grafted LLDPE (Bynel® CXA41E710). The barrier layer 146 has a thickness of about 4 μm, and is formed from a blend comprising about 85 wt. % amorphous polyamide (Selar® PA3426R) and about 15 wt. % functionalized rubber blend (Lotader® 4720). Each of the foam layer 2 (152) and the foam layer 3 (150) has a thickness of about 83 μm, and is formed from a blend comprising about 65 wt. % of hydrogenated vinyl-bond rich styrene-isoprene-styrene block copolymer (Hybrar® 7125), about 34 wt. % of EMA (EMAC® 2207), and about 1 wt. % of blowing agent (Safoam® FPE-20). The foam layer 1 (154) has a thickness of about 85 μm, and is formed from a blend comprising about 50 wt. % of hydrogenated vinyl-bond rich styrene-isoprene-styrene block copolymer (Hybrar® 7125), about 46 wt. % of EMA (Lotryl® 20MA08), about 2 wt. % of blowing agent (Safoam® FPE-20), and about 2 wt. % of slip and antiblock agent (Polybatch® SAB-1982VA). Thus, the composite film 140 of Sample X3300 has a total thickness of about 288 μm (11.3 mil).

Sample X3301 is also a seven-layer composite film 140 having the same layer construction as SampleX3299, which is illustrated in FIG. 4. The seal layer 142 has a thickness of about 25 μm, and is formed from a blend comprising about 50 wt. % of EMA (Lotryl® 20MA08), about 48 wt. % of PP-elastomers (Vistamaxx® 3980FL), and about 2 wt. % of a slip and antiblock agent (Polybatch® SAB-1982VA). Each of the tie layer 1 (148) and tie layer 2 (144) has a thickness of about 4 μm, and is formed from a blend comprising about 80 wt. % EMA (Lotryl® 18MA02) and about 20 wt. % MAH grafted LLDPE (Bynel CXA41E710). The barrier layer 146 has a thickness of about 4 μm, and is formed from a blend comprising about 85 wt. % amorphous polyamide (Selar® PA3426R) and about 15 wt. % functionalized rubber blend (Lotader® 4720). Each of the foam layer 2 (152) and the foam layer 3 (150) has a thickness of about 83 μm, and is formed from a blend comprising about 65 wt. % of hydrogenated vinyl-bond rich styrene-isoprene-styrene block copolymer (Hybrar® 7125), about 34 wt. % of EMA (EMAC® 2207), and about 1 wt. % of blowing agent (Expancel® 950MB80 from Akzo). The foam layer 1 (154) has a thickness of about 85 μm, and is formed from a blend comprising about 50 wt. % of hydrogenated vinyl-bond rich styrene-isoprene-styrene block copolymer (Hybrar® 7125), about 46 wt. % of EMA (Lotryl® 20MA08), about 2 wt. % of blowing agent (Expancel® 950MB80), and about 2 wt. % of slip and antiblock agent (Polybatch® SAB-1982VA). Thus, the composite film 140 of Sample X3301 has a total thickness of about 288 μm (11.3 mil).

The layers of Samples X3299, X3300, and X3301 were coextruded to form the composite film 140. Each layer was extruded using a separate extruder with appropriate settings for the particular polymer blend.

The control laminate had a thickness of about 11.3 mil, and included a PE nonwoven laminated to a six-layer odor barrier film with an adhesive between them. The six-layer odor barrier film had a thickness of about 2.24 mil (57 μm), and a seal layer/tie layer/barrier layer/tie layer/inner layer/seal layer construction. Each of the seal layers was formed from a blend of about 97.5% wt. EVA copolymer (Escorene® FL00218 available from ExxonMobil Corporation) and about 2.5 wt. % anti-block/slip additive (Polybatch® SAB1982VA available from Schulman Inc.) Each of the tie layers was formed from a blend of about 80 wt. % EMA (Lotryl® 18MA02) and about 20 wt. % MAH grafted LLDPE (Bynel® CXA41E710.) The barrier layer was formed from a blend of about 85 wt. % of an amorphous polyamide (Selar® PA3426R) and about 15 wt. % functionalized rubber blend (Lotader® 4720.) The inner layer was formed from a blend of about 87 wt. %-89.5 wt. % EVA copolymer (Escorene® FL00218) and about 10.5 wt. %-13 wt. % Schulman® T92030 Beige.

Mechanical properties of the sample composites and the control laminate were evaluated, and their data is summarized in Table 2.

TABLE 2

Mechanical Properties of Samples

|  |  | X3299 | X3300 | X3301 | Control |
|---|---|---|---|---|---|
| Actual Total Thickness (μm) |  | 280 | 288 | 294 | 280 |
| Elmendorf Tear at 800 mm (mN) | MD | 23154 | 24036 | 14058 | — |
|  | CD | 13327 | 15872 | 9847 | — |
| Elmendorf Tear at 800 mm (mN/mil) | MD | 2049 | 2127 | 1244 | — |
|  | CD | 1179 | 1405 | 871 | — |

TABLE 2-continued

Mechanical Properties of Samples

|  |  | X3299 | X3300 | X3301 | Control |
|---|---|---|---|---|---|
| Elmendorf Tear at 800 mm (gf/mil) | MD | 209 | 217 | 127 | — |
|  | CD | 120 | 143 | 89 | — |
| Tensile Strength (N/mm$^2$) | MD | 6.9 | 6.6 | 4.3 | 6.9 |
|  | CD | 6.7 | 6.5 | 4.0 | 2.8 |
| Tensile Strength (psi) | MD | 1000 | 951 | 626 | 1001 |
|  | CD | 965 | 937 | 586 | 405 |
| Tensile Yield (N/mm$^2$) | MD | 2.8 | 2.1 | 2.3 | 3.6 |
|  | CD | 2.3 | 2.2 | 1.7 | 2.5 |
| Tensile Yield (psi) | MD | 412 | 308 | 333 | 522 |
|  | CD | 327 | 312 | 245 | 356 |
| Elongation at Break (%) | MD | 628 | 746 | 532 | 254 |
|  | CD | 746 | 745 | 679 | 403 |
| Elongation at Yield (%) | MD | 42.9 | 37.9 | 32.4 | 137 |
|  | CD | 33.4 | 35.1 | 37.3 | 86 |
| Modulus (N/mm$^2$) | MD | 46.7 | 34.2 | 36.7 | 33.8 |
|  | CD | 37.8 | 32.8 | 26.5 | 26.2 |
| Modulus (ksi) | MD | 6.8 | 5.0 | 5.3 | 4.9 |
|  | CD | 5.5 | 4.8 | 3.8 | 3.8 |

The modulus data as shown in Table 2 indicate that Samples X3299, X3300, and X3301 have similar softness as the control laminate. The tensile strength data in machine direction (MD) and cross direction (CD) indicates that the control laminate has more anisotropicity. The elongation at break data indicates that Samples X3299, X3300, and X3301 are more ductile than the control laminate. Further, Samples X3299, X3300, and X3301 have good Elmendorf tear strength. Overall, the data indicates that Samples X3299, X3300, and X3301 have suitable mechanical properties for ostomy pouches.

Samples X3299, X3300, and X3301 and the control laminate were tested according to ASTM E2611-09 (Standard Test Method for Measurement of Normal Incidence Sound Transmission of Acoustical Materials Based on the Transfer Matrix Method) using Bruel & Kjaer Sound Impedance Tube Kit-Type 4206T. In this test, a sound source (e.g. loudspeaker) is mounted at one end of an impedance tube, and the sample is placed in a holder in the tube at a distance away from the sound source. The loudspeaker generates broadband, stationary random sound waves that propagate as plane waves. The plane waves hit the sample with part of the waves reflected back into the source tube, part absorbed by the laminate sample, and part passing through the sample to a receiving tube. By measuring the sound pressure at four fixed locations (two in the source tube and two in the receiving tube) and calculating the complex transfer function using a four-channel digital frequency analyzer, the transmission loss of the laminate sample is determined.

Figure 5:
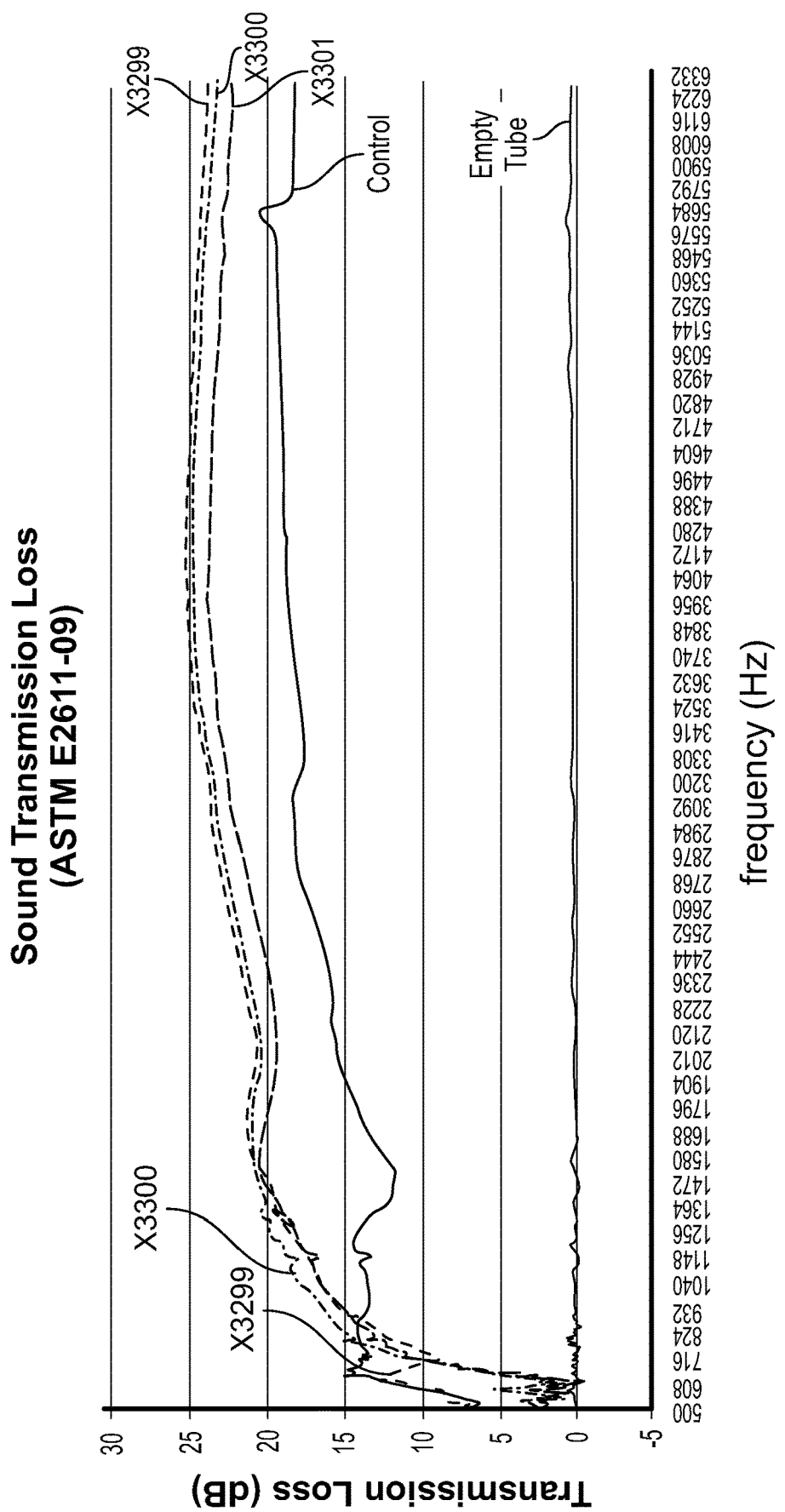
FIG. 5 is a graph showing sound transmission loss data for composite film samples.

The sound tube transmission loss test data for laminate samples are plotted and shown in FIG. 5. Transmission loss expressed in decibel (dB) shows the degree of sound reduced or absorbed by the samples. The most audible range of human hearing is between about 1,000 Hz to 4,000 Hz. As shown in FIG. 5, Samples X3299, X3300, and X3301 have significantly better sound reduction/absorption properties than the control laminate. For example, Samples X3299 and X3300 provided more sound reduction than the control laminated by more than about 6 dB at around 3,500-4,000 Hz frequencies. In ostomy applications, an improvement in the sound transmission loss of about 6 dB represents a significant reduction of embarrassing flatus gas noise.

Figure 8:
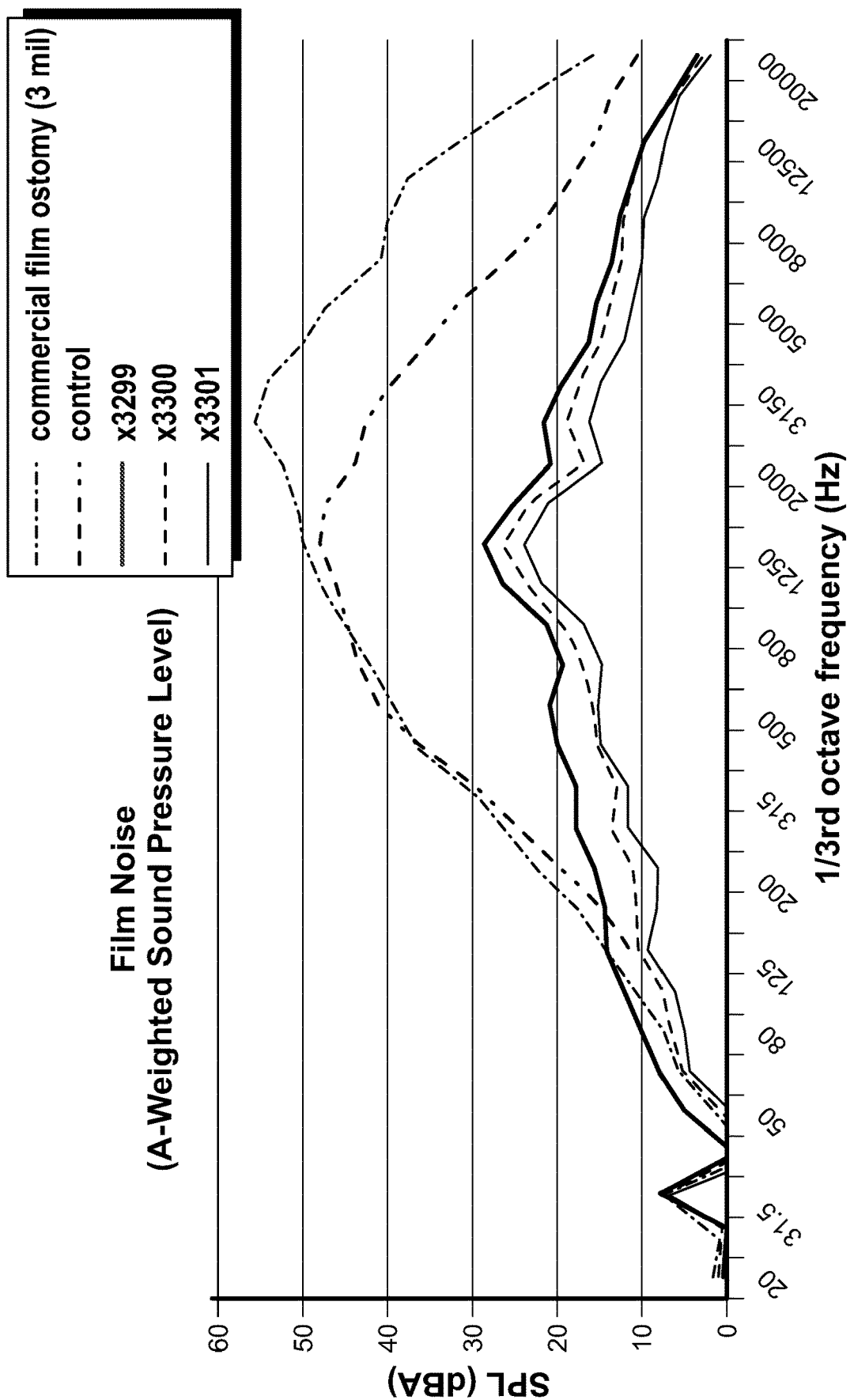
FIG. 8 is a graph showing film noise data in a-weighted sound pressure level for composite film samples.
Figure 9:
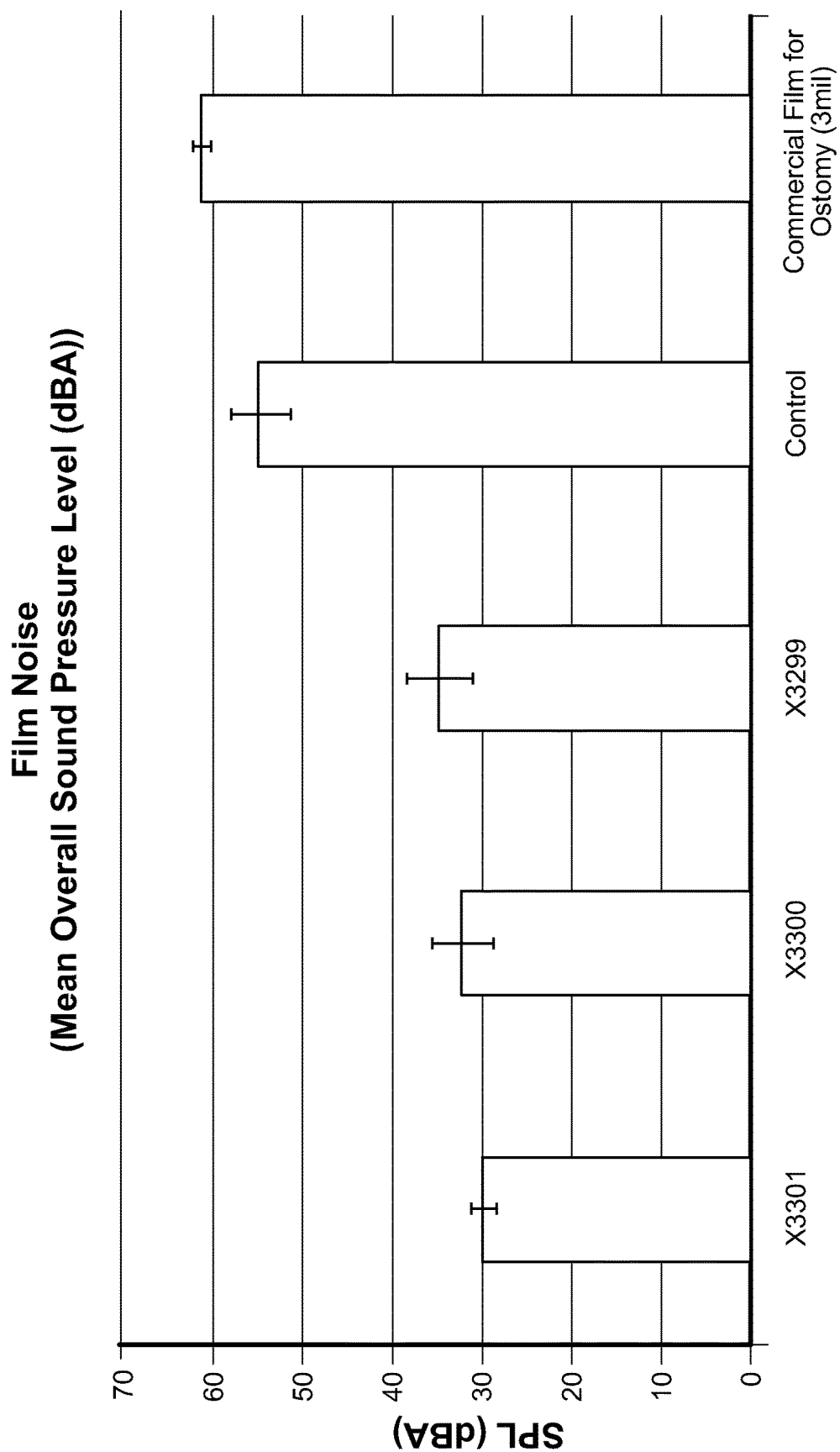
FIG. 9 is a graph showing film noise data in mean overall sound pressure level for composite film samples.

In addition to the sound absorbing properties, the laminate samples were also evaluated for film noise properties. The film noise properties are different than the sound absorbing properties in that the sound absorbing properties are indicative of sample's ability for reducing flatus noise, whereas the film noise properties are indicative of a level of noise produced by the sample itself, for example, crackling noise made by the sample. The film noise of the laminate samples were measured and plotted in FIGS. 8 and 9. FIG. 8 is a graph of a-weighted sound pressure level, and FIG. 9 is a graph of mean overall sound pressure level of the laminate samples, the control sample and a commercial film for ostomy pouch. The commercial film, which was a multilayer film including a barrier layer comprising vinylidene chloride-methyl acrylate copolymer, had a thickness of 3 mil. As can be seen in FIGS. 8 and 9, Samples X3299, X3300, and X3301 have significantly lower sound pressure levels than the control laminate and the commercial film. Thus, in addition to providing superior sound absorbing properties, the laminate samples also make less noise than the control laminate and the commercial film. That is, ostomy pouches made using the laminate samples can reduce flatus gas noise better, and are also quieter than those made using the control laminate or the commercial film.

Preferably, a composite film also includes at least one layer comprising a filler, such as talc, barium sulfate and/or mica, to further enhance sound absorbing properties. Two-layer laminate samples including a layer comprising barium sulfate or talc (Sample 302-2 and Sample 303-3) were prepared and evaluated for their sound absorbing properties. A two-layer control sample was also prepared. The compositions of the two-layer laminate samples and the control sample are summarized in Table 3.

(Vistamaxx® 3980FL), and about 2.0 wt. % of slip and antiblock agent (Polybatch® SAB-1982VA).

Figure 10:
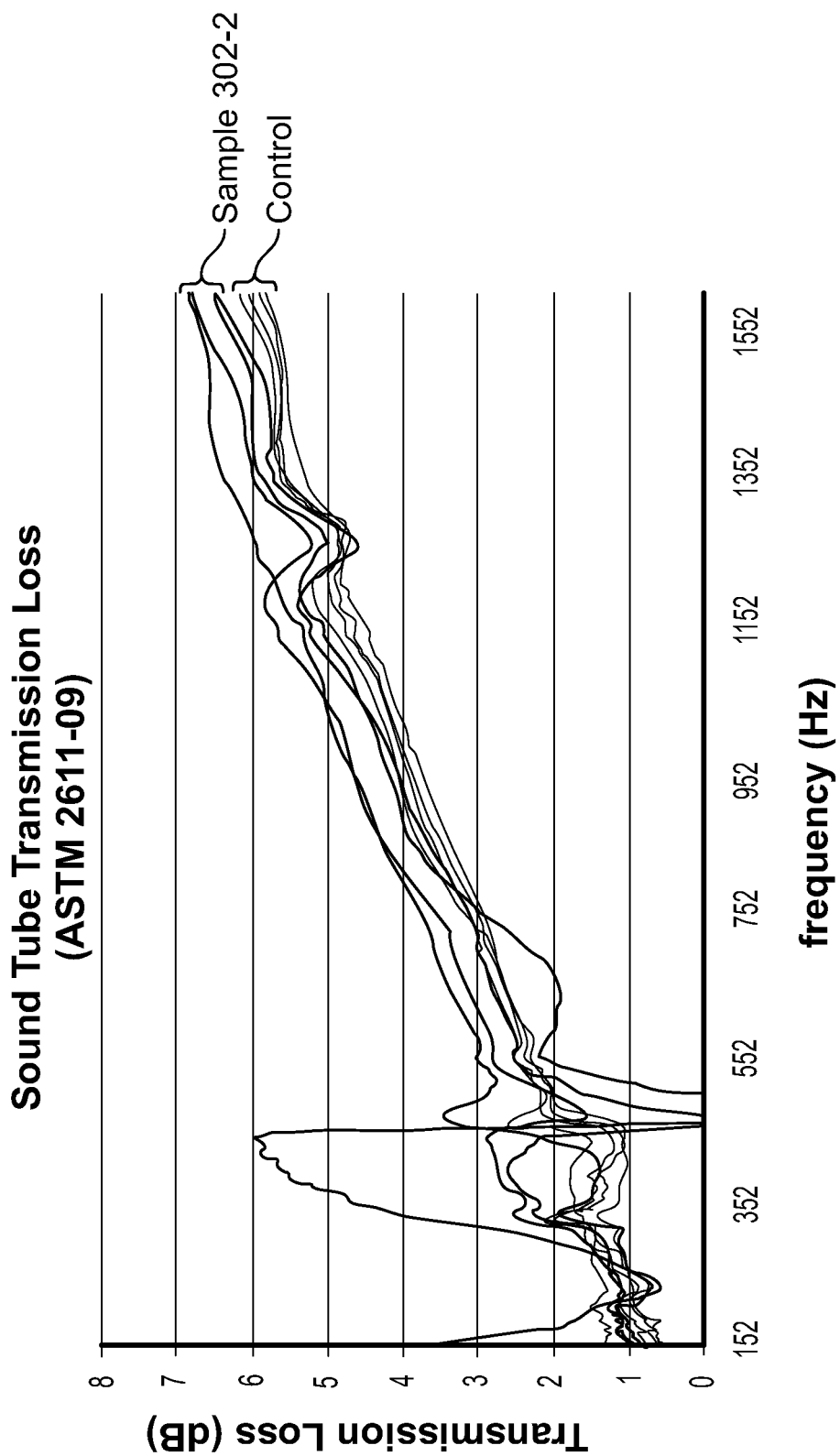
FIG. 10 is a graph showing sound transmission loss data for laminate samples including barium sulfate.
Figure 11:
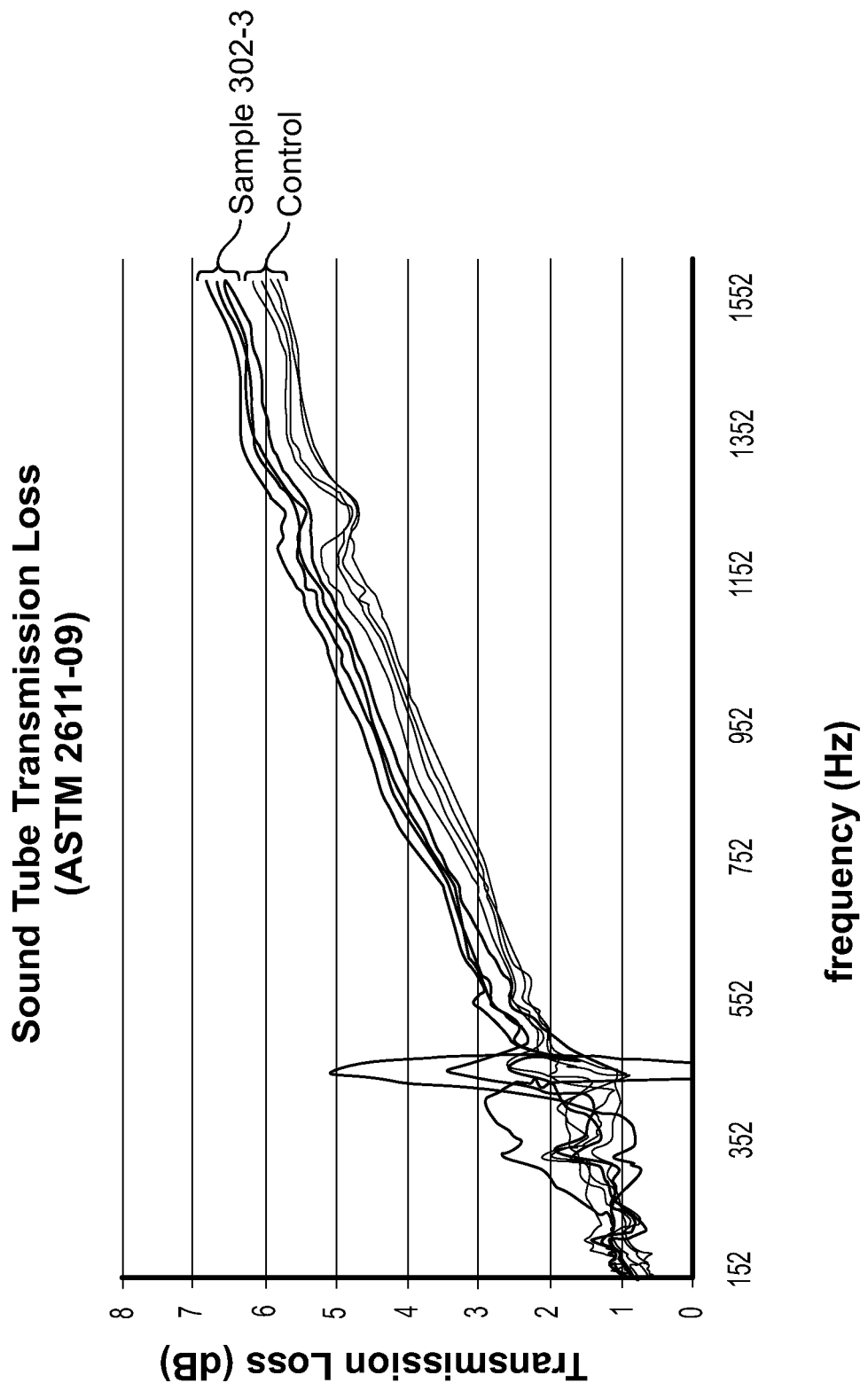
FIG. 11 is graph showing sound transmission loss data for laminate samples including talc.

Multiple samples of Sample 302-2, Sample 303-3, and Control were tested according to ASTM E2611-09. The sound tube transmission loss test data for these samples are plotted and shown in FIGS. 10 and 11. The sound transmission loss expressed in decibel (dB) shows the degree of sound reduced or absorbed by the samples. FIG. 10 shows the sound transmission loss data of Sample 302-2 samples and the control samples. FIG. 11 shows the sound transmission loss data of Sample 302-3 samples and the control samples. As shown in FIGS. 10 and 11, Sample 302-2 including a second layer comprising about 30 wt. % barium sulfate and Sample 302-3 including a second layer comprising about 30 wt. % talc have higher sound transmission loss data than the control samples, which did not include any filler. Thus, a composite film including at least one layer comprising a filler, such as barium sulfate or talc, can provide better sound absorbing properties than those that do not include a filler.

In the present disclosure, the words "a" or "an" are to be taken to include both the singular and the plural. Conversely, any reference to plural items shall, where appropriate, include the singular. All of the concentrations noted herein as percentage are percent by weight unless otherwise noted.

From the foregoing it will be observed that numerous modifications and variations can be effectuated without departing from the true spirit and scope of the novel concepts of the present invention. It is to be understood that no

TABLE 3

Laminate Samples and Control Sample

|  | First Layer (1 mil) | Second Layer (2 mil) |
|---|---|---|
| Control | 50.0 wt. % of Lotryl ® 20MA08 + 48.0 wt. % Vistamaxx ® 3980FL + 2.0 wt. % Polybatch ® SAB-1982VA | 60 wt. % Hybrar ® 5125 + 38 wt. % Lotryl ® 20MA08 + 2 wt. % Polybatch ® SAB-1982VA |
| Sample 302-2 | 20.0 wt. % of Lotryl ® 20MA08 + 48.0 wt. % Vistamaxx ® 3980FL + 30.0 wt. % Huberbrite ® HB1 + 2.0 wt. % Polybatch ® SAB-1982VA | 60 wt. % Hybrar ® 5125 + 38 wt. % Lotryl ® 20MA08 + 2 wt. % Polybatch ® SAB-1982VA |
| Sample 302-3 | 20.0 wt. % of Lotryl ® 20MA08 + 48.0 wt. % Vistamaxx ® 3980FL + 30.0 wt. % Luzenac ® HAR T-84 + 2.0 wt. % Polybatch ® SAB-1982VA | 60 wt. % Hybrar ® 5125 + 38 wt. % Lotryl ® 20MA08 + 2 wt. % Polybatch ® SAB-1982VA |

Each of the samples (Sample 302-2 and Sample 303-3) and the control sample had a total thickness of about 3 mil, and included a first layer having a thickness of about 1 mil and a second layer having a thickness of 2 mil. The second layer of Sample 302-2, Sample 303-3, and the control sample was formed of the same film comprising about 60 wt. % of a non-hydrogenated vinyl-bond rich styrene-isoprene-styrene block copolymer (Hybrar® 5125), about 38 wt. % of EMA (Lotryl® 20MA08), and about 2 wt. % of slip and antiblock agent (Polybatch® SAB-1982VA). The first layer of Sample 302-2 comprised about 20.0 wt. % of EMA (Lotryl® 20MA08), about 48.0 wt. % of PP-elastomers (Vistamaxx® 3980FL), about 30.0 wt. % barium sulfate (Huberbrite® HB1 from Huber), and about 2.0 wt. % of slip and antiblock agent (Polybatch® SAB-1982VA). The first layer of Sample 302-3 comprised about 20.0 wt. % of EMA (Lotryl® 20MA08), about 48.0 wt. % of PP-elastomers (Vistamaxx® 3980FL), about 30.0 wt. % talc (Luzenac® HAR T-84 from Imerys), and about 2.0 wt. % of slip and antiblock agent (Polybatch® SAB-1982VA). The first layer of the control sample comprised about 50.0 wt. % of EMA (Lotryl® 20MA08), about 48.0 wt. % of PP-elastomers limitation with respect to the specific embodiments illustrated is intended or should be inferred. The disclosure is intended to cover by the appended claims all such modifications as fall within the scope of the claims.

What is claimed is:

1. An ostomy pouch, comprising:
   an outer wall;
   a bodyside wall, wherein the outer wall and the bodyside wall are sealed along their peripheral edges to define a cavity; and
   wherein the bodyside wall is formed of a composite film including an outer foam layer, wherein the outer foam layer is a skin contact layer configured to provide comfort and softness characteristics that are comparable to a nonwoven comfort layer.

2. The ostomy pouch of claim 1, wherein the composite film further includes a seal layer and an odor barrier layer.

3. The ostomy pouch of claim 2, wherein the composite film has a six layer construction including seal layer/tie layer/odor barrier layer/tie layer/inner foam layer/outer foam layer or a seven layer construction including seal layer/tie layer/odor barrier layer/tie layer/foam layer/foam layer/outer foam layer.

4. The ostomy pouch of claim 2, wherein the layers of the composite film are coextruded.

5. The ostomy pouch of claim 1, wherein at least one of the foam layers includes a vinyl-bond rich triblock copolymer.

6. The ostomy pouch of claim 5, wherein each of the foam layers is formed from a blend comprising a non-hydrogenated vinyl-bond rich styrene-isoprene-styrene block copolymer and a polyolefin based material, or a blend comprising a hydrogenated vinyl-bond rich styrene-isoprene-styrene block copolymer and a polyolefin based material.

7. The ostomy pouch of claim 1, wherein the composite film further includes at least one layer comprising mica, barium sulfate, or talc.

8. A sound insulating ostomy pouch, comprising:
a first wall;
a second wall, wherein the first wall and the second wall are sealed along their peripheral edges to define a cavity; and
wherein at least one of the first wall and the second wall is formed of a composite film including at least one foam layer comprising a vinyl-bond rich triblock copolymer, wherein the vinyl-bond rich triblock copolymer has a tangent delta peak temperature of greater than about −20° C.

9. The sound insulating ostomy pouch of claim 8, wherein the at least one foam layer is formed from a blend comprising a non-hydrogenated vinyl-bond rich styrene-isoprene-styrene block copolymer and a polyolefin based material or a blend comprising a hydrogenated vinyl-bond rich styrene-isoprene-styrene block copolymer and a polyolefin based material.

10. The sound insulating ostomy pouch of claim 8, wherein the composite film further includes a seal layer and an odor barrier layer.

11. The sound insulating ostomy pouch of claim 10, wherein the composite film has a six layer construction including seal layer/tie layer/odor barrier layer/tie layer/inner foam layer/outer foam layer or a seven layer construction including seal layer/tie layer/odor barrier layer/tie layer/foam layer/foam layer/outer foam layer.

12. The sound insulated ostomy pouch of claim 8, wherein the at least one foam layer includes an outer foam layer, wherein the sound insulated ostomy pouch is configured such that the outer foam layer is in contact with user's skin when the sound insulated ostomy pouch is attached to the user, wherein the outer foam layer comprises a slip agent and has an open-cell construction.

13. The sound insulated ostomy pouch of claim 8, wherein the composite film further includes at least one layer comprising mica, barium sulfate, or talc.

14. The sound insulated ostomy pouch of claim 8, wherein each of the first wall and the second wall is formed of the composite film including at least one foam layer comprising a vinyl-bond rich triblock copolymer.

15. The sound insulated ostomy pouch of claim 8, wherein the first wall is a body side wall including an opening to receive stomal discharge, wherein the first wall is formed of the composite film including at least one foam layer, and a nonwoven layer attached to the first wall, such that the nonwoven layer is in contact with user's skin when the sound insulated ostomy pouch is attached to the user.

16. A sound insulating composite film including at least one foam layer comprising a vinyl-bond rich triblock copolymer, wherein the vinyl-bond rich triblock copolymer has a tangent delta peak temperature of greater than about −20° C.

17. The sound insulating composite film of claim 16, wherein the at least one foam layer is formed from a blend comprising a non-hydrogenated vinyl-bond rich styrene-isoprene-styrene block copolymer and a polyolefin based material, or a blend comprising a hydrogenated vinyl-bond rich styrene-isoprene-styrene block copolymer and a polyolefin based material.

18. The sound insulating composite film of claim 16, wherein the composite film further includes a seal layer and an odor barrier layer.

19. The sound insulating composite film of claim 18, wherein the composite film has a six layer construction including seal layer/tie layer/odor barrier layer/tie layer/inner foam layer/outer foam layer or a seven layer construction including seal layer/tie layer/odor barrier layer/tie layer/foam layer/foam layer/outer foam layer.

20. The sound insulating composite film of claim 16, wherein the composite film further includes at least one layer comprising mica, barium sulfate, or talc.

* * * * *